(12) United States Patent
Schleyer et al.

(10) Patent No.: US 7,476,506 B2
(45) Date of Patent: Jan. 13, 2009

(54) USE OF NRG4, OR INHIBITORS THEREOF, IN THE TREATMENT OF COLON AND PANCREATIC CANCERS

(75) Inventors: Siew C. Schleyer, El Cerrito, CA (US); Anne B. Jefferson, Oakland, CA (US); Judith A. Abraham, San Jose, CA (US); W. Michael Kavanaugh, Mill Valley, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 56 days.

(21) Appl. No.: 11/704,622

(22) Filed: Feb. 9, 2007

(65) Prior Publication Data

US 2007/0148691 A1 Jun. 28, 2007

Related U.S. Application Data

(62) Division of application No. 10/454,764, filed on Jun. 3, 2003, now Pat. No. 7,198,899.

(60) Provisional application No. 60/385,659, filed on Jun. 3, 2002, now abandoned.

(51) Int. Cl.
*C12Q 1/68* (2006.01)

(52) U.S. Cl. .................... 435/6; 435/7.21; 435/7.23; 530/387.7; 530/388.8; 530/389.7; 530/391.3; 530/350; 536/23.5; 536/24.3

(58) Field of Classification Search .............. 435/6, 435/7.21, 7.23; 530/350, 387.7, 388.8, 389.7, 530/391.3; 536/23.5, 24.3
See application file for complete search history.

(56) References Cited

U.S. PATENT DOCUMENTS

| | | | |
|---|---|---|---|
| 6,335,170 B1 | 1/2002 | Orntoft | |
| 6,387,638 B1 | 5/2002 | Ballinger et al. | |
| 6,544,759 B1 | 4/2003 | Harari et al. | |
| 6,825,333 B1 | 11/2004 | Kavanaugh et al. | |
| 6,936,417 B2 | 8/2005 | Orntoft | |
| 6,949,245 B1 | 9/2005 | Sliwkowski | |
| 7,041,292 B1 | 5/2006 | Sliwkowski | |
| 7,094,882 B2 | 8/2006 | Harari et al. | |
| 2002/0119148 A1 | 8/2002 | Gerritsen et al. | |
| 2003/0086924 A1 | 5/2003 | Sliwkowski | |
| 2003/0165843 A1 | 9/2003 | Shoshan et al. | |
| 2003/0204075 A9 | 10/2003 | Wang | |
| 2004/0013667 A1 | 1/2004 | Kelsey et al. | |
| 2004/0018522 A1 | 1/2004 | Dangond et al. | |
| 2004/0052786 A1 | 3/2004 | Gerritsen et al. | |
| 2004/0082510 A1 | 4/2004 | Ullrich et al. | |
| 2004/0121326 A1 | 6/2004 | Harai et al. | |
| 2004/0123343 A1 | 6/2004 | La Rosa et al. | |
| 2004/0248196 A1 | 12/2004 | Adams et al. | |
| 2005/0048491 A1 | 3/2005 | Weichselbaum et al. | |
| 2005/0208043 A1 | 9/2005 | Adams et al. | |
| 2005/0228172 A9 | 10/2005 | Wang | |
| 2005/0238640 A1 | 10/2005 | Sliwkowski | |
| 2006/0019888 A1 | 1/2006 | Zhou | |
| 2006/0034842 A1 | 2/2006 | Adams et al. | |
| 2006/0057564 A1 | 3/2006 | Wang | |
| 2006/0073143 A1 | 4/2006 | Adams et al. | |
| 2006/0083739 A1 | 4/2006 | Sliwkowski | |
| 2006/0093603 A1 | 5/2006 | Gerritsen et al. | |
| 2006/0134682 A1 | 6/2006 | Roberts et al. | |
| 2006/0141493 A1 | 6/2006 | West et al. | |
| 2006/0193854 A1 | 8/2006 | Adams et al. | |
| 2006/0198843 A1 | 9/2006 | Adams et al. | |
| 2006/0216285 A1 | 9/2006 | Adams et al. | |
| 2006/0257851 A1 | 11/2006 | Bentwich | |
| 2007/0009530 A1 | 1/2007 | Altaba et al. | |
| 2007/0015196 A1 | 1/2007 | Harari et al. | |

FOREIGN PATENT DOCUMENTS

| | | |
|---|---|---|
| EP | 1228766 | 8/2002 |
| JP | 2003510029 | 3/2003 |
| WO | WO 9805761 | 2/1998 |
| WO | WO 9918976 | 4/1999 |
| WO | WO 9965924 | 12/1999 |
| WO | WO 0052204 | 9/2000 |
| WO | WO 0100238 | 1/2001 |
| WO | WO 0100245 | 1/2001 |
| WO | PCT/US00/22326 | 3/2001 |
| WO | WO 01/14415 A2 | 3/2001 |
| WO | WO 0114415 | 3/2001 |
| WO | WO 0157182 | 8/2001 |
| WO | WO 0181540 | 11/2001 |
| WO | WO 0210449 | 2/2002 |
| WO | WO 0218444 | 3/2002 |
| WO | WO 0220756 | 3/2002 |
| WO | WO 0248191 | 6/2002 |
| WO | WO 02060470 | 8/2002 |
| WO | WO 02068579 | 9/2002 |
| WO | WO 03014159 | 2/2003 |
| WO | WO 03025142 | 3/2003 |
| WO | WO 03030719 | 4/2003 |
| WO | WO 03095618 | 11/2003 |
| WO | WO 03/101401 A2 | 12/2003 |
| WO | WO 03099300 | 12/2003 |
| WO | WO 03099320 | 12/2003 |
| WO | WO 03099321 | 12/2003 |

OTHER PUBLICATIONS

Hayes et al. (Oncogene. 2008; 27: 715-720).*

(Continued)

*Primary Examiner*—Stephen L Rawlings
(74) *Attorney, Agent, or Firm*—Lisa E. Alexander; Patricia Tsao

(57) ABSTRACT

This invention relates to compositions and uses of NRG4, and to variants thereof and to polynucleotides encoding NRG4, for therapeutic and diagnostic purposes, particularly related to colon and pancreatic cancer. This invention also relates to therapeutic agents based on or derived from the polynucleotides and proteins, NRG4 inhibitors, particularly antibodies capable of specifically binding to NRG4.

17 Claims, 2 Drawing Sheets

OTHER PUBLICATIONS

Hayes et al. (Clin. Cancer Res. 2007; 13 (11): 3147-3155).*
Carraway and Burden, "Neuregulins and their receptors," *Current Opinion in Neurobiology*, vol. 5, pp. 606-612, (1995).
Yarden and Sliwkowski, "Untangling the ErbB Signalling Network," *Nature Reviews, Molecular Cell Biology*, vol. 2, pp. 127-137. (2001).
Meyer and Birchmeier, "Multiple essential functions of neuregulin in development," *Nature*, vol. 378, pp. 386-390, (1995).
Carroll et al., "Expression of Neuregulins and their Putative Receptors, ErbB2 and ErbB3, Is Induced during Wallerian Degeneration," *The Journal of Neuroscience*, 17.5, pp. 1642-1659, (1997).
Burden and Yarden, "Neuregulins and Their Receptors: A Versatile Signaling Module in Organogenesis and Oncogenesis," *Neuron*, vol. 18, pp. 847-855, (1997).
Lee et al., "Requirement for neuregulin receptor erbB2 in neural and cardiac development," *Nature*, vol. 378, pp. 394-398, (1995).
Gassmann et al., "Aberrant neural and cardiac development in mice lacking the ErbB4 neuregulin receptor," *Nature*, vol. 378, pp. 390-394, (1995).
Carraway, "Involvement of the neuregulins and their receptors in cardiac and neural development," *BioEssays*, vol. 18, pp. 263-266, (1996).
Tzahar et al., "ErbB-3 and ErbB-4 Function as the Respective Low and High Affinity Receptors of All Neu differentiation Factor/Heregulin Isoforms," The Journal of Biological Chemistry, vol. 269, No. 40, pp. 25226-25233, (1994).
Pinkas-Kramarski et al., "ErbB Tyrosine Kinases and the Two Neuregulin Families Constitute a Ligand-Receptor Network," *Molecular and Cellular Biology*, vol. 18, No. 10, pp. 6090-6101, (1998).
Harari et al., "Neuregulin 4: a noval growth factor that acts through the ErbB-4 receptor tyrosine kinase," *Oncogene*, vol. 18, pp. 2681-2689, (1999).
Carraway III et al., "Heregulin Stimulates Mitogenesis and Phosphatidylinositol 3-Kinase in Mouse Fibroblasts Transfected with erbB2/neu and erbB3," *The Journal of Biological Chemistry*, vol. 270, No. 13, pp. 7111-7116, (1995).
Morrissey et al., "Axon-induced mitogenesis of human Schwann cells involves heregulin and p185erbB2," *Proc. Natl. Acad. Sci.*, vol. 92, pp. 1431-1435, (1995).
Peles and Yarden, "Neu and its Ligands: From an Oncogene to Neural Factors," *BioEssays*, vol. 15, pp. 815-824, (1993).
Marshall et al., "Neuregulins 1-4 are expressed in the cytoplasm or nuclei of ductal carcinoma (in situ) of the human breast," *Breast Cancer Research and Treatment*, vol. 96, pp. 163-168, (2006).
Dunn et al. (J Pathol. 2004; 203: 672-680).
Falls et al (Exp. Cell Res. 2003; 284: 14-30).
Harari et al. (Oncogene. 1999; 18: 2681-2689.
Gilmour et al. (Clin. Cancer Res. Dec. 8, 2002: 3933-3942).
GenBank Accession No. AA238077 dated Mar. 3, 1997, 2 pages.
Harari, D., et al., "Neuregulin-4: a novel growth factor that acts through the ErbB-4 receptor tyrosine kinase", Oncogene (1999) 18, pp. 2681-2689.
Starr, A., et al., "ErbB4 increases the proliferation potential of human lung cancer cells and its blockage can be used as a target for anti-cancer therapy", Cancer Cell Biology, 12 pages.
Yeda Research and Development Co., Ltd., "Neuregulin-4 (NRG4), a Novel Growth Factor Which Acts Through the Erbb4 Receptor Tyrosine Kinase; Sequences, Antibodies To and Uses Thereof." [online] [retrieved on 2006-08-2006]. Retrieved from the Internet.

* cited by examiner

SEQUENCE LISTING

<160> NUMBER OF SEQ ID NOS: 8

<210> SEQ ID NO 1
<211> LENGTH: 348
<212> TYPE: DNA
<213> ORGANISM: Homo sapiens

<400> SEQUENCE: 1

```
atgccaacag atcacgaaga gccctgtggt cccagtcaca agtcgttttg cctgaatggg      60
gggctttgtt atgtgatacc tactattccc agcccatttt gtaggtgcgt tgaaaactat     120
acaggagctc gttgtgaaga ggttttctc ccaggctcca gcatccaaac taaaagtaac      180
ctgtttgaag cttttgtggc attggcggtc ctagtaacac ttatcattgg agccttctac     240
ttcctttgca ggaaaggcca ctttcagaga gccagttcag tccagtatga tatcaacctg     300
gtagagacga gcagtaccag tgcccaccac agtcatgaac aacactga                  348
```

<210> SEQ ID NO 2
<211> LENGTH: 115
<212> TYPE: PRT
<213> ORGANISM: Homo sapiens

<400> SEQUENCE: 2

```
Met Pro Thr Asp His Glu Glu Pro Cys Gly Pro Ser His Lys Ser Phe
  1               5                  10                  15
Cys Leu Asn Gly Gly Leu Cys Tyr Val Ile Pro Thr Ile Pro Ser Pro
             20                  25                  30
Phe Cys Arg Cys Val Glu Asn Tyr Thr Gly Ala Arg Cys Glu Glu Val
         35                  40                  45
Phe Leu Pro Gly Ser Ser Ile Gln Thr Lys Ser Asn Leu Phe Glu Ala
     50                  55                  60
Phe Val Ala Leu Ala Val Leu Val Thr Leu Ile Ile Gly Ala Phe Tyr
 65                  70                  75                  80
Phe Leu Cys Arg Lys Gly His Phe Gln Arg Ala Ser Ser Val Gln Tyr
                 85                  90                  95
Asp Ile Asn Leu Val Glu Thr Ser Ser Thr Ser Ala His His Ser His
            100                 105                 110
Glu Gln His
        115
```

<210> SEQ ID NO 3
<211> LENGTH: 23
<212> TYPE: DNA
<213> ORGANISM: Artificial Sequence
<220> FEATURE:
<223> OTHER INFORMATION: Forward primer used to amplify NRG4

<400> SEQUENCE: 3

```
acagatcacg aagagccctg tgg                                              23
```

<210> SEQ ID NO 4
<211> LENGTH: 25
<212> TYPE: DNA
<213> ORGANISM: Artificial Sequence
<220> FEATURE:
<223> OTHER INFORMATION: Reverse primer used to amplify NRG4

<400> SEQUENCE: 4

```
ggtactgctc gtctctacca ggttg                                            25
```

<210> SEQ ID NO 5
<211> LENGTH: 24
<212> TYPE: DNA
<213> ORGANISM: Artificial Sequence
<220> FEATURE:
<223> OTHER INFORMATION: Forward primer used to amplify actin -continued

```
<400> SEQUENCE: 5
cgggaaatcg tgcgtgacat taag                                           24

<210> SEQ ID NO 6
<211> LENGTH: 24
<212> TYPE: DNA
<213> ORGANISM: Artificial Sequence
<220> FEATURE:
<223> OTHER INFORMATION: Reverse primer used to amplify actin

<400> SEQUENCE: 6
tgatctcctt ctgcatcctg tcgg                                           24

<210> SEQ ID NO 7
<211> LENGTH: 20
<212> TYPE: DNA
<213> ORGANISM: Artificial Sequence
<220> FEATURE:
<223> OTHER INFORMATION: Forward primer used to amplify GusB

<400> SEQUENCE: 7 cctttttgcga gagagatact                                               20

<210> SEQ ID NO 8
<211> LENGTH: 19
<212> TYPE: DNA
<213> ORGANISM: Artificial Sequence
<220> FEATURE:
<223> OTHER INFORMATION: Reverse primer used to amplify GusB

<400> SEQUENCE: 8
ccttagtgtt ccctgctag                                                 19
```

USE OF NRG4, OR INHIBITORS THEREOF, IN THE TREATMENT OF COLON AND PANCREATIC CANCERS

This application is a divisional and claims the benefit of priority under 35 U.S.C. § 120 of U.S. Ser. No. 10/454,764, filed Jun. 3, 2003, issued as U.S. Pat. No. 7,198,899, which claims benefit of U.S. Ser. No. 60/385,659, filed Jun. 3, 2002 (abandoned). The preceding applications are expressly incorporated herein by reference in its entirety.

BACKGROUND OF THE INVENTION

1. Field of the Invention

The present invention relates to nucleic acid sequences encoding a member of the neuregulin family, to polypeptides encoded by the nucleic acid sequences, inhibitors thereof, including antibodies and receptors that bind such polypeptides, and to their use in the treatment of colon and pancreatic cancer.

2. Description of the Related Art

Neuregulins (NRGs) belong to the epidermal growth factor (EGF) superfamily and are discussed in Carraway and Burden, *Curr. Opin. Neurobiol.* 5:1-7, 1995 and Yarden and Sliwkowski, *Nature Rev. Mol. Cell Biol.* 2:127-137, 2001. There is a need in the art for agents and methods useful in modulating members of the NRG family. Due to their crucial roles in several essential cellular functions, including proliferation and differentiation, NRGs are important therapeutic targets for a number of indications, including cancer, heart disease, wound healing, neurodegenerative diseases, and brain injury.

BRIEF SUMMARY OF THE INVENTION

The invention provides a composition comprising an isolated antibody that binds specifically to an NRG4 polypeptide, wherein the isolated antibody preferentially binds to NRG4 but not to other NRGs.

In preferred embodiments, the antibody is monoclonal, polyclonal or a single-chain antibody.

Another object of the invention is to provide a method for detecting NRG4 polypeptides or mRNA for diagnostic and prognostic purposes.

In a preferred embodiment, the method utilizes an antibody which binds an NRG4 polypeptide, and comprises contacting the antibody under binding conditions with a biological sample from a human suspected of having an NRG4 protein-modulated disorder, and determining the amount of duplex formed between the antibody and the NRG4 protein in the biological sample, compared to a normal sample.

In another preferred embodiment, the method utilizes a polynucleotide that binds to mRNA encoding an NRG4 polypeptide under stringent conditions, such method comprising contacting nucleic acid of the biological sample with the polynucleotide under binding conditions to form a duplex, and determining the amount of the duplex formed, compared to a normal sample.

Another object of the invention is to provide methods of modulating the amount of NRG4 protein activity in a subject, using NRG4 polypeptide, NRG4-encoding polynucleotide, polypeptides representing NRG4 antisense, and NRG4 antibody or receptor compositions.

In one embodiment, the method comprises administering an effective amount of a composition comprising an NRG4 polypeptide or an antibody that binds to an NRG4 polypeptide.

In another embodiment, the method comprises administering an effective amount of a composition consisting of an NRG4-encoding polynucleotide, or a polynucleotide complementary to all or part of natural mRNAs encoding NRG4 polypeptides.

A further object of the invention is to provide methods for treating an NRG4 protein-modulated disorder in a subject, using an NRG4 polypeptide, NRG4-encoding polynucleotide, polynucleotides complementary to NRG4 encoding polynucleotides, or NRG4 antibody compositions.

In one embodiment, the method comprises administering an effective amount of a composition comprising an NRG4 polypeptide or an antibody that binds to an NRG4 polypeptide of the invention, wherein the composition further comprises a pharmaceutically acceptable carrier.

In another embodiment, the method comprises administering an effective amount of a composition consisting of an NRG4-encoding polynucleotide or polynucleotide representing NRG4 antisense, a ribozyme, or RNAi, wherein the composition further comprises a pharmaceutically acceptable carrier.

In a preferred embodiment, the method is accomplished by implanting cells containing a polynucleotide encoding an NRG4 polypeptide of the invention into the patient, wherein the cells express NRG4 polypeptide in the patient, and wherein the implanted cells optionally contain a heterologous or recombinant DNA expression construct for expressing NRG4 polypeptide.

In a most preferred embodiment, the implanted cells are encapsulated in a semipermeable membrane.

In another embodiment of the invention, a patient is treated with a therapeutically effective amount of a polynucleotide capable of hybridizing to an NRG4-encoding polynucleotide or complement thereof.

In preferred embodiments, the polynucleotide is an antisense construct, a ribozyme, or RNAi.

In another preferred embodiment, the polynucleotide is a viral, such as a retroviral, vector comprising a promoter and an NRG4-encoding polynucleotide or a complement thereof.

In yet another embodiment a patient is treated with a therapeutically effective amount of a polypeptide capable of binding an NRG4 polypeptide.

In a most preferred embodiment, the polypeptide is an antibody.

In another preferred embodiment, the polypeptide is a wild-type or mutant receptor for NRG4.

The invention further provides a method for diagnosing a NRG4 protein-modulated disorder using a biological sample from a human suspected of having the disorder, the method comprising:

(a) providing an antibody that binds to an NRG4 polypeptide;

(b) contacting the antibody with the sample under binding conditions to form a duplex; and (c) determining the amount of duplex formed, compared to a normal sample.

The invention also provides a method for diagnosing a NRG4 protein-modulated disorder in a biological sample from a human suspected of having the disorder, the method comprising:

(a) providing a polynucleotide that binds to mRNA encoding an NRG4 polypeptide under stringent conditions;

(b) contacting nucleic acid of the sample with the polynucleotide under binding conditions to form a duplex; and (c) determining the amount of the duplex formed, compared to a normal sample.

The invention still further provides a method for modulating the amount of NRG4 protein activity in a subject, the method comprising administering an effective amount of a composition selected from a group consisting of:
(a) an NRG4 polypeptide;
(b) an antibody that binds to an NRG4 polypeptide; and
(c) a wild-type or mutant receptor for NRG4.

The invention further provides a method for modulating the amount of a NRG4 protein in a subject, comprising administering an effective amount of a composition comprising a polynucleotide encoding NRG4.

The invention further provides a method for treating an NRG4 protein-modulated disorder in a subject, comprising administering to the subject an effective amount of a composition selected from a group consisting of:
(a) an NRG4 polypeptide;
(b) an antibody that binds an NRG4 polypeptide; and
(c) a wild-type or mutant receptor for NRG4, wherein the composition further comprises a pharmaceutically acceptable carrier.

The invention also provides a method for treating a NRG4 protein-modulated disorder in a subject, comprising administering to the subject an effective amount of a composition consisting of an NRG4 polynucleotide (sense or antisense), wherein the composition further comprises a pharmaceutically acceptable carrier.

The invention further provides a method of providing trophic support for cells in a patient in need thereof, the method comprising administering to the patient a composition selected from the group consisting of a polynucleotide encoding an NRG4 polypeptide comprising SEQ ID NO:2, and an NRG4 polypeptide. The composition may additionally or alternatively comprise fragments of NRG4 polypeptide, such as amino acids 1-45; 2-45, or 9-45.

In one embodiment, the polynucleotide is administered by implanting cells which express the polynucleotide into the patient, wherein the cells express NRG4 polypeptide in the patient, and in a specific embodiment the implanted cells are encapsulated in a semipermeable membrane.

In a further embodiment of this method, the patient suffers from a condition selected from the group consisting of pancreatic cancer and colon cancer.

In specific embodiments of this method, the polynucleotide is an antisense construct, ribozyme, RNAi, or a viral vector comprising a promoter.

The invention yet further provides a method of treating a patient with an NRG4 protein-modulated disorder, such as colon cancer, the method comprising administering a composition comprising a therapeutically effective amount of polypeptides capable of binding NRG4 or a variant thereof.

In a specific embodiment of this method, the polypeptides are antibodies.

BRIEF DESCRIPTION OF THE SEQUENCES

Figure 1:
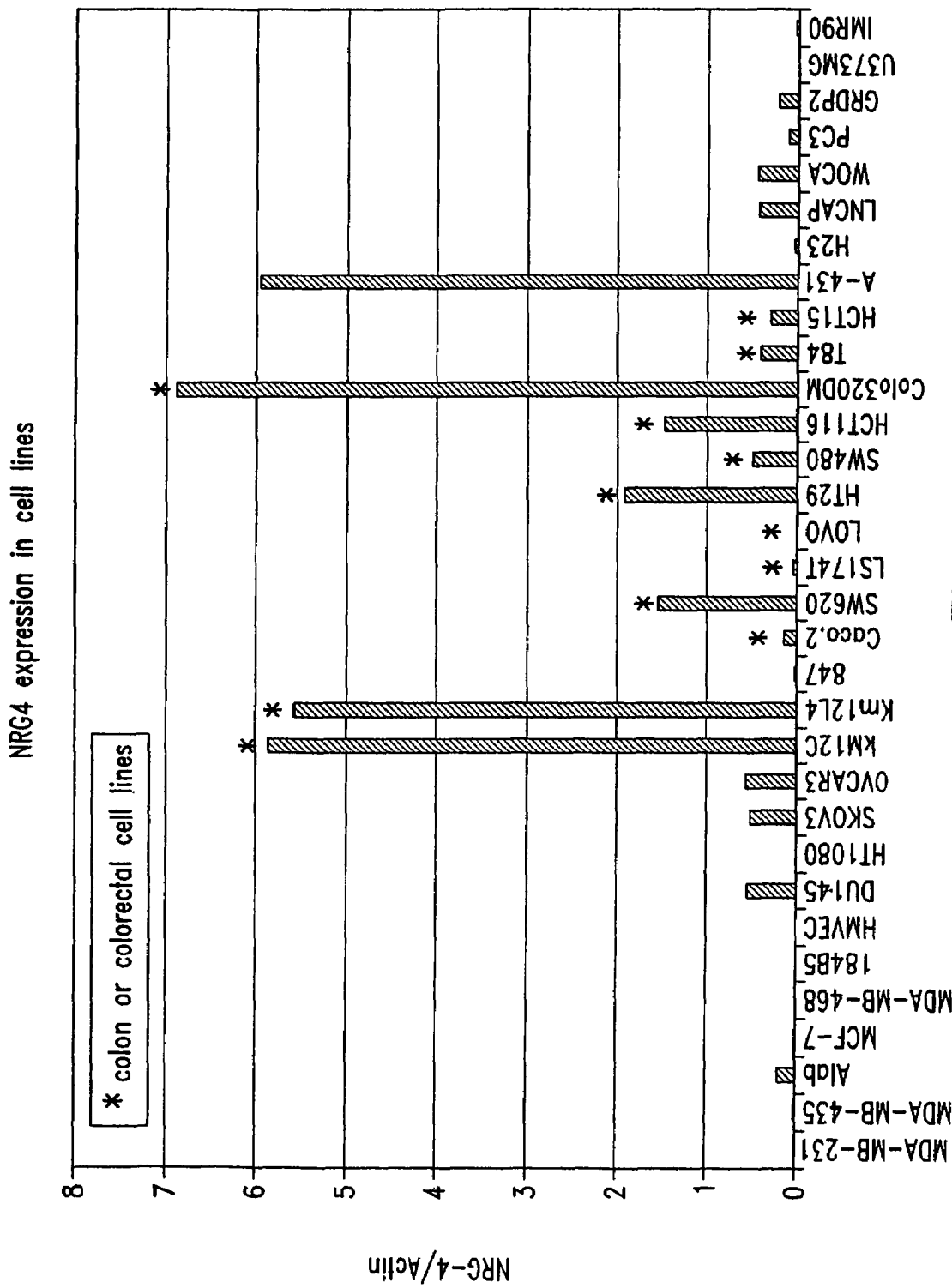
FIG. 1 is a bar graph showing expression of NRG4 in a variety of cell lines, relative to actin expression.

SEQ ID NO:1 is the polynucleotide sequence of NRG4.
SEQ ID NO:2 is the amino acid sequence of NRG4.
SEQ ID NO:3 is the forward primer used to amplify NRG4.
SEQ ID NO:4 is the reverse primer used to amplify NRG4.
SEQ ID NO:5 is the forward primer used to amplify actin.
SEQ ID NO:6 is the reverse primer used to amplify actin.
SEQ ID NO:7 is the forward primer used to amplify GusB.
SEQ ID NO:8 is the reverse primer used to amplify GusB.

DETAILED DESCRIPTION OF THE INVENTION

Neuregulins are a family of structurally related polypeptides, members of which regulate cellular proliferation, differentiation, apoptosis, and cell survival (reviewed in Carraway and Burden, *Curr. Opin. Neurobiol* 5:1-7, 1995). In vivo studies demonstrated that targeted disruption of the neuregulin-1 gene is associated with cardiac and neural abnormalities, indicating that neuregulins play an important role in cardiac and neural development (Meyer and Birchmeier, *Nature* 378:386-390, 1995). Furthermore, expression and signaling by certain neuregulin family members was altered following nerve injury and degeneration (Carroll et al., *J. Neurosc.* 17:1642-1659, 1997). Thus, neuregulins are important therapeutic targets for a number of indications, including, for example, cancers such as breast cancer, prostate cancer, pancreatic cancer, colon cancer and ovarian cancer; heart diseases and injuries such as myocardial infarction and ischemia; wound healing such as bone fractures, tissue repair and regeneration; skin conditions such as burns, cuts, and ulcers; neurological conditions such as neuro-degenerative disease and stroke, multiple sclerosis, peripheral neuropathy, amyotrophic lateral sclerosis, dementia, Alzheimer's disease, Parkinson's disease, and Huntington's disease, brain injury, acute spinal cord injury, nervous system injury and peripheral nerve injury; infection, epilepsy, and acoustic trauma.

Neuregulins mediate cellular responses through interactions with their receptors, transmembrane tyrosine kinases of the ErbB family (reviewed in Burden and Yarden, *Neuron* 18:847-855, 1997). These receptors function as homo- and heterodimers. Different receptor combinations exhibit different binding affinities for neuregulins and different abilities to activate downstream signaling complexes and promote cell proliferation. Neuregulin-1 (NRG1) and neuregulin-2 (NRG2) bind directly to the ErbB3 and ErbB4 receptor but can recruit ErbB1 and ErbB2 as coreceptors. Targeted disruption in mice of the genes encoding ErbB2 and ErbB4 results in heart malformations and defects in the nervous system (Lee et al., *Nature* 378:386-390, 1995; Gassmann et al., *Nature* 378:390-394, 1995). However, the specific neural defects differ between ErbB2 and ErbB4 homozygous mutant mice (Carraway, *BioEssays* 18:263-266, 1996). These findings demonstrate that specific receptors play different roles in cell growth and development.

The neuregulins constitute a subfamily of the epidermal growth factor (EGF) family. Neuregulins contain a characteristic receptor-binding EGF-like motif with six conserved cysteine residues. Neuregulin precursors may contain other motifs, including a signal peptide, a cysteine-containing N-terminal domain, either a cysteine-rich domain (CRD) or a domain distantly related to a kringle motif, an Ig-like loop, a glycosylation domain, and a transmembrane domain (Burden and Yarden, *Neuron* 18:847-855, 1997). Depending on the presence or absence of the transmembrane domain, neuregulin precursors may be either transmembrane proteins or secreted polypeptides. The most highly conserved region of neuregulins is their EGF-like domain.

Four members of the neuregulin family have been identified, including NRG1, NRG2, NRG3, and NRG4. Multiple isoforms of NRG1 and NRG2 exist, some of which display heterogeneous binding affinities for different ErbB receptors (Tzahar et al., *J. Biol. Chem.* 269:25226-25233, 1994; Pinkas-Kramarski et al., *Mol. Cell Biol.* 18:6090-6101, 1998). The different NRG1 isoforms result from alternative splicing of a single gene (Carraway, *BioEssays* 18:263-266, 1996). The present invention employs NRG4 polypeptides and polynucleotides encoding NRG4. NRG4 is disclosed in applicants' co-pending application PCT/US00/22326. NRG4 is expressed in specific tissues during development and promotes meiotic maturation of Xenopus oocytes. In humans, NRG4 is expressed in particular in skeletal muscle and pancreas cells, and NRG4 levels are altered in pancreatic tumor tissue as compared to normal pancreatic samples.

NRG4 Nucleic Acids, Polypeptides and Antibodies.

The nucleotide sequence encoding a cDNA copy of the coding region for NRG4 is shown in SEQ ID NO:1. The predicted polypeptide sequence for NRG4 is shown in SEQ ID NO:2. These sequences were first disclosed in applicants' co-pending application PCT/US00/22326.

Polynucleotide molecules of the invention can be made using the techniques of synthetic chemistry given the sequences disclosed herein. The degeneracy of the genetic code permits alternate nucleotide sequences to be synthesized which will encode the amino acid sequence of SEQ ID NO:2. Use of all such nucleotide sequences is within the scope of the present invention.

The present invention employs nucleic acid sequences that encode NRG4. Also included within the scope of the methods of the invention are sequences that are substantially the same as the nucleic acid sequences encoding NRG4. Such substantially same sequences may, for example, be substituted with codons more readily expressed in a given host cell such as *E. coli* according to well known and standard procedures. The present invention also employs nucleic acid sequences that will hybridize to sequences which encode NRG4 or complements thereof. Such nucleic acid sequences can be at least 90%, 91%, 92%, 93% or 94% identical, preferably 95%, 96%, 97%, 98% or 99% identical. The invention employs nucleic acid sequences encoding functional domains of NRG4. In addition, the invention employs nucleic acids that encode polypeptides that are recognized by antibodies that bind NRG4 polypeptides. Polynucleotides encoding such polypeptides can range in size from 10, 25, 50, 75, 125, 150, 175, 200, 225, 250, 275, 300, 325, 335, or 345 contiguous nucleotides of SEQ ID NO:1, although this list is not intended to be limiting and intermediate lengths may also be suitable.

The present invention employs vectors comprising expression regulatory elements operably linked to any of the nucleic acid sequences employed within the scope of the invention. Vectors may include, but are not limited to, plasmids, episomes, retroviruses, lentivirus, adenovirus, and parvoviruses including adeno-associated virus. This invention also employs host cells, of any variety, that have been transformed or infected or transfected with vectors comprising expression regulatory elements operably linked to any of the nucleic acid sequences included within the scope of the present invention. Examples of host cells include bacterial cells, yeast cells, plant cells, tissue culture cells including primary, immortalized and transformed cell lines, and insect cells.

Reference to NRG4 herein is intended to include growth factors of any origin which are substantially homologous to and which are biologically equivalent to the NRG4 characterized and described herein. Such substantially homologous growth factors may be native to any tissue or species and, similarly, biological activity can be characterized in any of a number of biological assay systems. For example, assays for measuring NRG4 activity are disclosed in PCT/US00/22326 and Harari et al., *Oncogene* 18:2681-2689, 1999, both of which are incorporated by reference herein.

The term "biologically equivalent" is intended to mean that the compositions of the present invention are capable of demonstrating some or all of the same growth properties in a similar fashion, not necessarily to the same degree as the NRG4 as described herein or recombinantly produced NRG4 of the invention.

The invention also employs fragments of NRG4. Preferred fragments include: amino acids from about residue 9 to about residue 45 as shown in SEQ ID NO:2; amino acids from about residue 4 to about residue 50; amino acids from about residue 4 to about residue 82; amino acids from about residue 1 or 2 to residue 50; amino acids about residue 1 or 2 to residue 64; and amino acids from about residue 1 or 2 to about residue 82 as shown in SEQ ID NO: 2. Such fragments can be prepared from the protein by standard biochemical methods or by expressing a polynucleotide encoding the fragment.

Also employed within the scope of the invention are NRG4 molecules that differ from native NRG4 by virtue of changes in biologically active sites. NRG4 has a putative transmembrane domain at amino acid residues 64-82. An NRG4 molecule that does not include this transmembrane domain can be prepared by expressing DNA encoding NRG4, wherein the corresponding codons for some or all of amino acid residues 64-82 have been deleted. DNA encoding NRG4 with altered receptor binding can likewise be produced. The EGF-like receptor binding domain of NRG4 extends from approximately amino acid 4 to amino acid 50, more particularly from about amino acid 9 to about amino acid 45. For example, it may be desirable to alter receptor specificity of NRG4 by substituting the receptor binding regions of a different neuregulin or other EGF-like domain for that of NRG4.

Also included within the meaning of substantially homologous is any NRG4 which may be isolated by virtue of cross-reactivity with antibodies to the NRG4 described herein or whose encoding nucleotide sequences including genomic DNA, mRNA or cDNA may be isolated through hybridization with the complementary sequence of genomic or subgenomic nucleotide sequences or cDNA of the NRG4 herein or fragments thereof. It will also be appreciated by one skilled in the art that degenerate DNA sequences can encode NRG4 and these are also intended to be included within the methods and compositions of the present invention, as are allelic variants of NRG4.

Recombinant NRG4 may be made by expressing the DNA sequences encoding NRG4 in a suitable transformed host cell. Using methods well known in the art, the DNA encoding NRG4 may be incorporated into an expression vector, transformed into a host cell and conditions established that are suitable for expression of NRG4 by the transformed cell.

The DNA encoding NRG4 can be engineered to take advantage of preferred codon usage of host cells. Codon usage in *Pseudomonas aeruginosa* is described in, for example, West et al., *Nucleic Acids Res.* 11:9323-9335, 1988. Codon usage in *Saccharomyces cerevisiae* is described in, for example, Lloyd et al., *Nucleic Acids Res.* 20:5289-5295, 1992. Codon preference in Corynebacteria and a comparison with *Escherichia coli* preference is provided in Malubres et al., *Gene* 134:15-24, 1993. Codon usage in *Drosophila melanogaster* is described in, for example, Akashi, *Genetics* 136: 927-935, 1994.

Any suitable expression vector may be employed to produce recombinant NRG4. For example, insect cells such as Baculovirus can also be employed as expression systems. A preferred method is expression in insect cells, such as Tn5 or Sf9 cells, using baculovirus vector. Other methods can include *E. coli*, yeast cells, etc.

The invention employs polypeptide fragments of NRG4. Polypeptide fragments of the invention can comprise at least 8, 10, 12, 15, 18, 19, 20, 25, 50, 55, 60, 65, 70, 75, 80, 85, 90, 95, 100, 105, 110, or 112 contiguous amino acids selected from SEQ ID NO:2.

Exemplary 20 amino acid fragments include the following based on SEQ ID NO:2: 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100, 82-101, 83-102, 84-103, 85-104, 86-105, 87-106, 88-107, 89-108, 90-109, 91-110, 92-111, 93-112, 94-113, 95-114, and 96-115.

Exemplary 25 amino acid fragments include the following based on SEQ ID NO:2: 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88-112, 89-113, 90-114,and 91-115.

Biologically Active Variants

Variants of the protein and polypeptides disclosed herein can also be employed in the invention. Variants can be naturally or non-naturally occurring. Naturally occurring variants are found in humans or other species and comprise amino acid sequences which are substantially identical to the amino acid sequence shown in SEQ ID NO:2. Species homologs of the protein can be obtained using subgenomic polynucleotides of the invention or fragments thereof as suitable probes or primers to screen cDNA libraries from other species, such as mice, monkeys, or yeast, identifying cDNAs which encode homologs of the protein, and expressing the cDNAs as is known in the art.

Non-naturally occurring variants, which retain substantially the same biological activities as naturally occurring protein variants, are also included here. Preferably, naturally or non-naturally occurring variants have amino acid sequences which are at least 85%, 90%, or 95% identical to the amino acid sequence shown in SEQ ID NO:2. Harari et al., *Oncogene* 18:2681-2689 (1999), disclose methods for assaying NRG4 activity, including binding to ErbB proteins, signal activation, stimulation of proliferation of ErbB-4-expressing cells, and recognition and activation of ErbB-4. Biological activities of EGFH2 proteins are also disclosed in PCT/US00/22326, including mitogenic effects.

More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

Guidance in determining which amino acid residues can be substituted, inserted, or deleted without abolishing biological or immunological activity can be found using computer programs well known in the art, such as DNASTAR software. Preferably, amino acid changes are conservative amino acid changes, i.e., substitutions of similarly charged or uncharged amino acids. A conservative amino acid change involves substitution between members of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, glycine, phenylalanine, methionine, tryptophan), and uncharged polar (asparagine, glutamine, cysteine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310, 1990.

Variants of the NRG4 protein used herein include glycosylated forms, aggregative conjugates with other molecules, and covalent conjugates with unrelated chemical moieties. Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

The invention further employs variations of the NRG4 polypeptide which show comparable expression patterns to those disclosed herein in relation to pancreatic and colon cancer, or which include antigenic regions. Such mutants include deletions, insertions, inversions, repeats, and type substitutions.

Of particular interest are substitutions of basic or positively charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because aggregates can be immunogenic. (Pinckard et al., *Clin. Exp. Immunol.* 2:331-340 1967; Robbins et al., *Diabetes* 36:838-845, 1987; Cleland et al., *Crit. Rev. Therapeutic Drug Carrier Systems* 10:307-377, 1993).

Amino acids in the NRG4 polypeptides employed in the present invention that are essential for function can be identified by methods known in the art, such as site-directed mutagenesis or alanine-scanning mutagenesis (Cunningham and Wells, *Science* 244:1081-1085,1989). The latter procedure introduces single alanine mutations at many, if not every residue position in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904, 1992; and de Vos et al. *Science* 255:306-312, 1992).

Antibodies to NRG4

Antibodies to NRG4 are employed in the invention. Antibodies of the invention can be used, for example, to detect NRG4 polypeptides on cells, in culture medium, or in biological samples, such as blood or tissue samples. Antibodies may be polyclonal, monoclonal or single chain antibodies. Antibodies to NRG4 protein or an epitope thereof can be made by any of a number of methods known in the art. Detailed methods for generating antibodies are provided in Harlow and Lane, Antibodies: A Laboratory Manual, Cold Spring Harbor Laboratories, 1988, which is incorporated by reference. Methods of generating the antibodies are also described in U.S. patent application Ser. No. 08/988,671, which is incorporated by reference in its entirety. By epitope, reference is made to an antigenic determinant of a polypeptide. An epitope could comprise at least 6, 7, 8, 9, 10, or 11 amino acids in a spatial conformation which is unique to the epitope. Methods of determining the spatial conformation of amino acids are known in the art, and include, for example, x-ray crystallography and 2 dimensional nuclear magnetic resonance. Antibodies to NRG4 can also be raised against oligopeptides that include one or more conserved regions such that the antibody can cross-react with other species and/or family members.

Polyclonal antibodies can be prepared by immunizing rabbits or other animals by injecting antigen followed by subsequent boosts with antigen at appropriate intervals. Animal sera is assayed for immunoreactivity against NRG4 by any of a number of methods, including, for example, Western blot or ELISA. Monoclonal antibodies can be prepared after the method of Milstein and Kohler by fusing splenocytes from immunized mice or other animals, such as rats or rabbits, with continuously replicating tumor cells (Milstein and Kohler, *Nature* 256:495-497, 1975).

Techniques for purifying antibodies are those available in the art. In a preferred embodiment, antibodies are affinity purified by passing the antibodies over a column to which amino acid sequences of the invention are bound. Bound antibody is then eluted. Any technique may be chosen to purify antibodies of the invention.

Methods well known in the art may be used to generate antibodies, polyclonal antisera, or Monoclonal antibodies that are specific for an NRG4 polypeptide. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second, distinct mammalian species. Most commonly, a chimeric antibody has murine variable region sequences and human constant region sequences. Such a murine/human chimeric immunoglobulin may be "humanized" by grafting the complementarity determining regions (CDRs) derived from a murine antibody, which confer binding specificity for an antigen, into human-derived V region framework regions and human-derived constant regions. Fragments of these molecules may be generated by proteolytic digestion, or optionally, by proteolytic digestion followed by mild reducton of disulfide bonds and alkylation. Alternatively, such fragments may also be generated by recombinant genetic engineering techniques.

As used herein, an antibody is said to be "immunospecific" or to "specifically bind" an NRG4 polypeptide if it reacts at a detectable level with the NRG4, preferably with an affinity constant, $K_a$, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci. USA* 51:660 (1949)) or by surface plasmon resonance (BIAcore, Biosensor, Piscataway, N.J.) (Wolff et al., *Cancer Res.* 53:2560-65 (1993).

Antibodies may generally be prepared by any of a variety of techniques known to those having ordinary skill in the art. See, e.g., Harlow et al., *Antibodies: A Laboratory Manual*, Cold Spring Harbor Laboratory (1988). In one such technique, an animal is immunized with an NRG4 polypeptide as an antigen to generate polyclonal antisera. Suitable animals include, for example, rabbits, sheep, goats, pigs, cattle, and may also include smaller mammalian species, such as mice, rats, and hamsters, or other species.

Human monoclonal antibodies may be generated by any number of techniques with which those having ordinary skill in the art will be familiar. Such methods include but are not limited to, Epstein Barr Virus (EBV) transformation of human peripheral blood cells (e.g., containing B lymphocytes) (see, e.g., U.S. Pat. No. 4,464,456); in vitro immunization of human B cells (Boerner et al., *J. Immunol.* 147:86-95 (1991)); fusion of spleen cells from immunized transgenic mice carrying human immunoglobulin genes inserted by yeast artificial chromosomes (YAC) (U.S. Pat. No. 5,877,397; Bruggemann et al., *Curr. Opin. Biotechnol.* 8:455-58 (1997); Jakobovits et al., *Ann. N. Y. Acad. Sci.* 764:525-35 (1995)); isolation from human immunoglobulin V region phage libraries (U.S. Pat. No. 5,223,409; Huse et al., *Science* 246:1275-81 (1989), Kang et al., *Proc. Natl. Acad. Sci. USA* 88:4363-66 (1991); Hoogenboom et al., *J. Molec. Biol.* 227:381-88 (1992); Schlebusch et al., *Hybridoma* 16:47-52 (1997) and references cited therein), or other procedures as known in the art and based on the disclosure herein.

Chimeric antibodies, specific for an NRG4 polypeptide, including humanized antibodies, may also be generated according to the present invention. A chimeric antibody has at least one constant region domain derived from a first mammalian species and at least one variable region domain derived from a second, distinct mammalian species. See, e.g., Morrison et al., *Proc. Natl. Acad. Sci. USA*, 81:6851-55 (1984). In preferred embodiments, a chimeric antibody may be constructed by cloning the polynucleotide sequence that encodes at least one variable region domain derived from a non-human monoclonal antibody, such as the variable region derived from a murine, rat, or hamster monoclonal antibody, into a vector containing a nucleic acid sequence that encodes at least one human constant region. See, e.g., Shin et al., *Methods Enzymol.* 178:459-76 (1989); Walls et al., *Nucleic Acids Res.* 21:2921-29 (1993). Another method known in the art for generating chimeric antibodies is homologous recombination (e.g., U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such a humanized antibody may comprise a plurality of CDRs derived from an immunoglobulin of a non-human mammalian species, at least one human variable framework region, and at least one human immunoglobulin constant region. Humanization may in certain embodiments provide an antibody that has decreased binding affinity for an NRG4 polypeptide when compared, for example, with either a non-human monoclonal antibody from which an NRG4 polypeptide binding variable region is obtained, or a chimeric antibody having such a V region and at least one human C region, as described above. See, e.g., Jones et al., *Nature* 321:522-25 1(986); Riechmann et al., *Nature* 332:323-27 (1988); Padlan et al., *FASEB* 9:133-39 (1995); Chothia et al., *Nature,* 342: 377-383 (1989); Bajorath et al., *Ther. Immunol.* 2:95-103 (1995); EP-0578515-A3.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or protein G, or immobilized NRG4 polypeptide, or a suitable variant or fragment thereof. Those having ordinary skill in the art can routinely and without undue experimentation determine what is a suitable variant or fragment based on characterization of affinity purified antibodies obtained, for example, using immunodetection methods as provided herein. An alternative method to generate Fab fragments includes mild reduction of F(ab')$_2$ fragments followed by alkylation. See, e.g., Weir, *Handbook of Experimental Immunology,* Blackwell Scientific, Boston (1986).

According to certain embodiments, non-human, human, or humanized heavy chain and light chain variable regions of any of the above-described Ig molecules may be constructed as single chain Fv (sFv) polypeptide fragments (single chain antibodies). See, e.g., Bird et al., *Science* 242:423-26 (1988); Huston et al., *Proc. Natl. Acad. Sci. USA* 85:5879-83 (1988).

An NRG4-binding immunoglobulin (or fragment thereof) as described herein may contain a detectable moiety or label such as an enzyme, cytotoxic agent, or other reporter molecule, including a dye, radionuclide, luminescent group, fluorescent group, or biotin, or the like. The NRG4-specific immunoglobulin or fragment thereof may be radiolabeled for diagnostic or therapeutic applications. Techniques for radiolabeling of antibodies are known in the art. See, e.g., Adams, *In Vivo* 12:11-21 (1998); Hiltunen, *Acta Oncol.* 32:831-39 (1993). Therapeutic applications are described in greater detail below and may include use of the NRG4-binding antibody (or fragment thereof) in conjunction with other therapeutic agents. The antibody or fragment may also be conjugated to a cytotoxic agent as known in the art and provided herein, for example, a toxin, such as a ribosome-inactivating protein, a chemotherapeutic agent, an anti-mitotic agent, an antibiotic or the like.

The invention also contemplates the generation of anti-idiotype antibodies that recognize an antibody (or antigen-binding fragment thereof) that specifically binds to an NRG4 polypeptide as provided herein, or a variant or fragment thereof. Anti-idiotype antibodies may be generated as polyclonal antibodies or as monoclonal antibodies by the methods described herein, using an anti-NRG4 antibody (or antigen-binding fragment thereof) as immunogen. Anti-idiotype antibodies or fragments thereof may also be generated by any of the recombinant genetic engineering methods described above, or by phage display selection. An anti-idiotype antibody may react with the antigen binding site of the anti-NRG4 antibody such that binding of the anti-NRG4 antibody to an NRG4 polypeptide is competitively inhibited. Alternatively, an anti-idiotype antibody as provided herein may not competitively inhibit binding of an anti-NRG4 antibody to an NRG4 polypeptide.

As provided herein and according to methodologies well known in the art, polyclonal and monoclonal antibodies may be used for the affinity isolation of NRG4 polypeptides. See, e.g., Hermanson et al., *Immobilized Affinity Ligand Techniques,* Academic Press, Inc. New York (1992). Briefly, an antibody (or antigen-binding fragment thereof) may be immobilized on a solid support material, which is then contacted with a sample comprising the polypeptide of interest (e.g., an NRG4 polypeptide). Following separation from the remainder of the sample, the polypeptide is then released from the immobilized antibody.

Antibodies to NRG4 may find use in treatment of patients with colon cancer, in view of the upregulation of NRG4 in colon cancer cell lines as disclosed herein. Antibodies to NRG4 may also find use in modulating effects of NRG4 that are mediated through binding of NRG4 to its receptor, erbB-4.

Therapeutic and Diagnostic Uses of NRG4.

Members of the neuregulin family influence cellular proliferation, differentiation, and apoptosis. For example, neuregulin-1 stimulates mitogenesis of mouse fibroblasts, human Schwann cells, epithelial and glial cells (Carraway et al., *J. Biol. Chem.* 270:7111-7116, 1995; Morrissey et al., *Proc. Natl. Acad. Sci. U.S.A.* 92:1431-1435, 1995; Peles and Yarden, *Bioessays* 15:815-824, 1993). Neuregulin-1 also acts as a survival factor for astrocytes (Pinkas-Kramarski et al., *Proc. Natl. Acad. Sci. U.S.A.* 91:9387-9391, 1994). Thus, neuregulins regulate cell growth and tissue homeostasis and represent important targets for treatment of diseases associated with aberrant cell growth, such as cancer, tumor progression, hyperproliferative cell growth or accompanying biological or physical manifestations. NRG4 is a neuregulin family member which regulates cell proliferation.

Neuregulins are expressed in tissue- and stage-specific patterns. Neuregulin-1 isoforms are primarily expressed in neural and muscle tissue (discussed in Carraway, *Bioessays* 18:263-266, 1996). According to the present invention, real time polymerase chain reaction (PCR) analysis revealed that NRG4 is expressed at an elevated level in approximately 50% of the colon/colorectal cell lines tested compared to normal colon. In addition, of the normal tissues tested, all except pancreas and skeletal muscle demonstrated low levels of NRG4. Thus, according to the invention, NRG4 is likely to play a role in colon cancer.

Colon cancer may be treated using inhibitors or other modulators of NRG4. Alternatively or in addition, NRG4 may be used as a differentiation factor to treat the cancer directly.

The present invention includes methods of treating patients in need thereof with NRG4-encoding polynucleotides and NRG4 polypeptides. NRG4 was downregulated in five pancreatic cancer cell lines. Thus, diseases and disorders which can be treated using compositions of the present invention include, but are not limited to, cancers including pancreatic cancer.

The present invention includes therapeutic or pharmaceutical compositions comprising NRG4-encoding polynucleotides and NRG4 polypeptides. Pharmaceutical compositions can comprise polypeptides, antibodies, small molecules or polynucleotides. Therapeutics, whether polynucleotide or polypeptide or small molecule, can be tested, for example, in animal models and cell lines disclosed in Bosland, *Encyclopedia of Cancer,* volume II, pages 1283 to 1296 and 1303 to 1313 (1997) by Academic Press. Pharmaceutical compositions may be designed to either decrease or increase NRG4 activity, depending on the type of disease or disorder being treated. For example, cancers or diseases associated with hyperproliferation may be treated by reducing NRG4 activity, for example, by administering therapeutically effective amounts of antisense NRG4 RNA, NRG4 ribozymes, RNAi specific for NRG4, inactivating antibodies, peptide or small molecule antagonists or inhibitors, NRG4 mutants or NRG4 receptors or mutants thereof. However, conditions or diseases that can be treated by promoting cell proliferation may be treated, for example, by administering biologically active NRG4 polypeptides or an expression vector comprising NRG4 polynucleotides encoding biologically active NRG4 polypeptides.

The term "therapeutically effective amount" as used herein refers to an amount of a therapeutic agent to treat, ameliorate, or prevent a specific disease or condition, or to exhibit a detectable therapeutic or preventive effect. The effect can be detected by, for example, chemical markers or antigen levels. The effects also include reduction in physical symptoms. The effective amount for a given situation can be determined by routine experimentation and is within the judgment of the clinician. The precise effective amount will vary depending on factors including, but not limited to, the subject's size and health, the nature and extent of the condition, and the therapeutics selected for administration. For purposes of the present invention, an effective dose will be from about 0.05 mg/kg to 50 mg/kg or 0.05 mg/kg to about 10 mg/kg of the polynucleotide, polypeptide or antibody compositions in the individual to which it is administered.

A pharmaceutical composition can also contain a pharmaceutically acceptable carrier. The term "pharmaceutically acceptable carrier" refers to a carrier for administration of a therapeutic agent, such as antibodies, polypeptides, polynucleotides and other therapeutic agents. Suitable carriers and pharmaceutically acceptable salts are well known to those of ordinary skill in the art. A thorough discussion of pharmaceutically acceptable excipients is available in *Remington's Pharmaceutical Sciences* (Mack Pub. Co., N.J. 1991).

Once formulated, the polynucleotide and polypeptide compositions of the invention can be (1) administered directly to the subject; (2) delivered ex vivo, to cells derived from the subject; or (3) delivered in vitro for expression of recombinant proteins. Direct delivery of the compositions will generally be accomplished by injection, subcutaneously, intraperitoneally, intravenously, intra-arterially or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in, e.g., International Publication No. WO 93/14778. Generally, delivery of nucleic acids for both ex vivo and in vitro applications can be accomplished by, for example, dextran-mediated transfection, calcium phosphate precipitation transfection, viral infection, polybrene mediated transfection, protoplast fusion, electroporation, encapsulation of the polynucleotide(s) in liposomes, and direct microinjection of the DNA into nuclei, all well known in the art.

Examples of polynucleotide therapeutic agents include ribozymes, antisense RNA, and mammalian expression vectors. Trans-cleaving catalytic RNAs (ribozymes) are RNA molecules possessing endoribonuclease activity. Ribozymes are engineered to cleave any RNA species site-specifically in the background of cellular RNA. The cleavage event renders the target RNA unstable and prevents protein expression. Ribozyme design and therapeutic uses are disclosed in Usman et al., *Current Opin. Struct. Biol.* 6:527-533, 1996, which is incorporated by reference. The NRG4 polynucleotide sequence provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the NRG4 polynucleotide coding sequence. These monomeric and multimeric ribozymes are tested in vitro for an ability to cleave the NRG4 mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

The present invention also relates to antisense oligonucleotides designed to interfere with the normal function of NRG4 polynucleotides. Any modifications or variations of the antisense molecule which are known in the art to be broadly applicable to antisense technology are included within the scope of the invention. Such modifications include preparation of phosphothioate linkages, with increased stability, as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases as disclosed in U.S. Pat. No. 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. The level of the target mRNA in the cell can be measured routinely in treated and control cells by reverse transcription of the mRNA with or without PCR amplification and assaying the resulting cDNA levels. The biological effect of antisense delivery to cells can be determined routinely by measuring cell growth or viability as is known in the art.

Measuring the specificity of antisense activity by generating, assaying and analyzing cDNA levels is an art-recognized method of validating antisense results. For example, RNA from treated and control cells can be reverse-transcribed and the resulting cDNA populations analyzed. (Branch, A. D., *T.I.B.S.* 23:45-50, 1998.).

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected sequence can interfere with expression of the corresponding gene. Antisense polynucleotides are typically generated within the cell by expression from antisense constructs that contain the antisense strand as the transcribed (product) strand. Antisense polynucleotides can bind and/or interfere with the translation of the corresponding mRNA. The expression products of control cells and cells treated with the antisense construct are compared to detect the effects of the antisense polynucleotide on the protein product of the gene corresponding to the polynucleotide. The protein is detected and identified using routine biochemical methods.

Antisense therapy for a variety of cancers is in clinical phase and has been discussed extensively in the literature. Given the extensive background literature and clinical experience in antisense therapy, one skilled in the art can use antisense NRG4 polynucleotides as therapeutics. The dosage and means of administration are determined based on the specific qualities of the composition, the patient, the progression of the disease and other relevant factors. Preferably, the therapeutic antisense composition contains an expression construct comprising a promoter upstream of a polynucleotide segment of at least 12, 18, 20, 22, 25, 30, or 35 contiguous nucleotides of NRG4 in the antisense orientation. Therapeutic antisense agents may be administered locally or systemically by a variety of methods known in the art. Examples cited include those mentioned above and receptor-mediated targeted delivery.

Therapeutic compositions containing antisense NRG4 polynucleotides are administered in a range of about 100 ng to about 200 mg of polynucleotides for local administration in a gene therapy protocol, as discussed later. In all cases, routine experimentation in clinical trials will determine specific ranges for optimal therapeutic effects.

The invention also contemplates introduction of RNA with partial or fully double-stranded character into the cell or into the extracellular environment. Inhibition is specific to the NRG4 expression in that a nucleotide sequence from a portion of the target NRG4 gene is chosen to produce inhibitory RNA. This process is (1) effective in producing inhibition of gene expression, and (2) specific to the targeted NRG4 gene. The procedure may provide partial or complete loss of function for the target NRG4 gene. A reduction or loss of gene expression in at least 99% of other targeted cells has been shown using such methods. In certain embodiments, the target cell containing the target NRG4 gene may be a pancreatic cell of a human, or a pancreatic tumor cell of a human. Lower doses of injected material and longer times after administration of dsRNA may result in inhibition in a smaller fraction of cells. Quantitation of gene expression in a cell may show similar amounts of inhibition at the level of accumulation of target mRNA or translation of target protein. Methods of preparing and using RNAi are generally disclosed in U.S. Pat. No. 6,506,559, incorporated herein by reference.

The RNA may comprise one or more strands of polymerized ribonucleotide; it may include modifications to either the phosphate-sugar backbone or the nucleoside. The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. RNA containing a nucleotide sequence identical to a portion of the NRG4 target gene is preferred for inhibition. RNA sequences with insertions, deletions, and single point mutations relative to the target sequence have also been found to be effective for inhibition. Thus, sequence identity may be optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region may be used to transcribe the RNA strand (or strands).

For RNAi, the RNA may be directly introduced into the cell (i.e., intracellularly); or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected. Physical methods of introducing nucleic acids include injection directly into the cell or extracellular injection into the organism of an RNA solution.

The advantages of the method include the ease of introducing double-stranded RNA into cells, the low concentration of RNA which can be used, the stability of double-stranded RNA, and the effectiveness of the inhibition.

Inhibition of gene expression refers to the absence (or observable decrease) in the level of protein and/or mRNA product from a NRG4 target gene. Specificity refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 20%, 30%, 50%, 60%, 70%, 80%, 90%, 95% or 99% as compared to a cell not treated according to the present invention. Lower doses of injected material and longer times after administration of dsRNA may result in inhibition in a smaller fraction of cells (e.g., at least 10%, 20%, 50%, 75%, 90%, or 95% of targeted cells). Quantitation of NRG4 gene expression in a cell may show similar amounts of inhibition at the level of accumulation of NRG4 target mRNA or translation of NRG4 target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

The RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

RNA containing a nucleotide sequences identical to a portion of the NRG4 target gene are preferred for inhibition. RNA sequences with insertions, deletions, and single point mutations relative to the target sequence may be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the NRG4 target gene is preferred. Alternatively, the duplex region of the RNA may be defined functionally as a nucleotide sequence that is capable of hybridizing with a portion of the NRG4 target gene transcript (e.g., 400 mM NaCl, 40 mM PIPES pH 6.4, 1 mM EDTA, 50° C. or 70° C. hybridization for 12-16 hours; followed by washing). The length of the identical nucleotide sequences may be at least 25, 50, 100, 200, 300 or 400 bases.

100% sequence identity between the RNA and the NRG4 target gene is not required to practice the present invention. Thus the methods have the advantage of being able to tolerate sequence variations that might be expected due to genetic mutation, strain polymorphism, or evolutionary divergence.

NRG4 RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (for example, WO 97/32016; U.S. Pat. Nos. 5,593,874, 5,698,425, 5,712,135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellullady into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food is engineered to express the RNA, then fed to the organism to be affected. For example, the RNA may be sprayed onto a plant or a plant may be genetically engineered to express the RNA in an amount sufficient to kill some or all of a pathogen known to infect the plant. Physical methods of introducing nucleic acids, for example, injection directly into the cell or extracellular injection into the organism, may also be used. Vascular or extravascular circulation, the blood or lymph system, and the cerebrospinal fluid are sites where the RNA may be introduced. A transgenic organism that expresses RNA from a recombinant construct may be produced by introducing the construct into a zygote, an embryonic stem cell, or another multipotent cell derived from the appropriate organism.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

The RNAi may be used alone or as a component of a kit having at least one of the reagents necessary to carry out the in vitro or in vivo introduction of RNA to test samples or subjects. Preferred components are the dsRNA and a vehicle that promotes introduction of the dsRNA. Such a kit may also include instructions to allow a user of the kit to practice the invention.

Suitable injection mixes are constructed so animals receive an average of $0.5 \times 10^6$ to $1.0 \times 10^6$ molecules of RNA. For comparisons of sense, antisense, and dsRNA activities, injections are compared with equal masses of RNA (i.e., dsRNA at half the molar concentration of the single strands). Numbers of molecules injected per adult are given as rough approximations based on concentration of RNA in the injected material (estimated from ethidium bromide staining) and injection volume (estimated from visible displacement at the site of injection). A variability of several-fold in injection volume between individual animals is possible.

Polypeptide compositions can also include antibodies and peptides. The effective dosages, for therapeutic compositions containing protein, polypeptide or antibody are in the range of about 10 μg to about 50 μg/kg of patient body weight, about 50 μg to about 5 mg/kg, about 100 μg to about 500 μg/kg of patient body weight, and about 200 to about 250 μg/kg.

Antibodies may be polyclonal, monoclonal or single-chain antibodies prepared by methods known in the field. Antibodies specific to NRG4 polypeptides bind the protein and inhibit the protein from functioning in the cell. For example, the antibodies can prevent NRG4 from binding to binding partners or receptors. The invention also pertains to antibodies directed against protein partners and receptors for NRG4 polypeptides. Such antibodies can disrupt protein:protein interactions required for cellular function of NRG4. They can also inhibit downstream signaling by the receptor protein.

Therapeutic compositions and methods comprising peptide-agonists and antagonists are also included in the invention. The peptides can affect the function of polypeptides encoded by NRG4 mRNA or their binding partners and receptors. For example, the peptides may block protein:protein interactions or cause conformational changes which diminish or enhance NRG4's normal functional activity. The peptides may also alter NRG4's activity or specificity in a therapeutically useful manner.

The therapeutic polynucleotides of the present invention may be utilized in gene delivery vehicles. The gene delivery vehicle may be of viral or non-viral origin (see generally, Jolly, *Cancer Gene Therapy* 1:51-64, 1994; Kimura, *Human Gene Therapy* 5:845-852, 1994; Connelly, *Human Gene Therapy* 1:185-193, 1995; and Kaplitt, *Nature Genetics* 6:148-153, 1994). Gene therapy vehicles for delivery of constructs including a coding sequence of NRG4 can be administered either locally or systemically. Expression of such coding sequences can be driven using endogenous mammalian or heterologous promoters. Expression of the coding sequence can be either constitutive or regulated.

Any gene delivery method known in the art can be utilized. For example, the present invention can employ recombinant retroviruses that are constructed to carry or express a selected nucleic acid molecule of interest. The present invention also employs alphavirus-based vectors and parvovirus, which can function as gene delivery vehicles. Other gene delivery vehicles and methods may be employed, including polycationic condensed DNA linked or unlinked to killed adenovirus alone, for example Curiel, *Hum. Gene Ther.* 3:147-154, 1992; ligand linked DNA, for example see Wu, *J. Biol. Chem.* 264:16985-16987, 1989; eukaryotic cell delivery vehicles, for example see U.S. Ser. No. 08/240,030, filed May 9, 1994, and U.S. Pat. No. 6,015,686; deposition of photopolymerized hydrogel materials; hand-held gene transfer particle gun, as described in U.S. Pat. No. 5,149,655; ionizing radiation as described in U.S. Pat. No. 5,206,152 and in WO92/11033; nucleic charge neutralization or fusion with cell membranes. Additional approaches are described in Philip, *Mol. Cell Biol.* 14:2411-2418, 1994, and in Woffendin, *Proc. Natl. Acad. Sci.* 91:11581-11585, 1994. Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles.

Non-viral delivery methods include, but are not limited to, mechanical delivery systems such as the approach described in Woffendin et al., *Proc. Natl. Acad. Sci. USA* 91(24):11581-11585, 1994, and naked DNA protocols. Exemplary naked DNA introduction methods are described in WO 90/11092 and U.S. Pat. No. 5,580,859.

Subgenomic NRG4 polynucleotides and complements thereof and NRG4 antibodies can be used as markers to diagnose and determine the prognosis of cancer, tumor progression, hyperproliferative cell growth or accompanying biological and physical manifestations. Levels of NRG4 polynucleotides or polypeptides in a sample are compared to the levels in a normal control sample. The normal sample can include a pool of cells from a particular tissue or tissues and/or cells from throughout the body. Immunoassays or nucleic acid assays can be used for such measurements. Any observed difference between the sample and normal control can indicate the occurrence of disease or disorder. Typically, if the levels of NRG4 polynucleotides or polypeptides are higher or lower than those found in the normal control, the results can indicate the occurrence of cancer, tumor progression, hyperproliferative cell growth and/or accompanying biological or physical manifestations.

Nucleic acid assays utilize subgenomic polynucleotides capable of hybridizing under stringent conditions to NRG4 polynucleotides or complements thereof. Polynucleotide probes comprising at least 10, 25, 50 contiguous nucleotides or more selected from the nucleotide sequence of NRG4 are labeled, for example, with a radioactive, fluorescent, biotinylated, or chemiluminescent label, and detected by well known methods appropriate for the particular label selected. Subgenomic polynucleotides are preferably intron-free. Polynucleotides corresponding to NRG4 can be introduced into vectors and propagated in suitable hosts. Plasmids can be introduced into host cells using techniques available in the art. These techniques include, but are not limited to, electroporation and calcium phosphate-mediated transfection. They can be isolated and purified from DNA vectors by standard techniques, such as restriction enzyme digestion and gel electrophoresis or chromatography. The polynucleotides can also be produced using the polymerase chain reaction according to techniques well known in the art.

By "stringent conditions" is meant, for example, hybridization stringency conditions of wash conditions with 2×SSC, 0.1% SDS, room temperature twice, 30 minutes each; then 2×SSC, 0.1% SDS, 50° C. once, 30 minutes; then 2×SCC, room temperature twice, 10 minutes each. Hybridization is affected by a variety of parameters including temperature, salt concentration, formamide concentration, and length of probe. Some guidelines regarding hybridization conditions are as follows: (a) the higher the temperature, the more specific the hybridization; (b) lower salt concentrations mean higher stringency at any one temperature; (c) formamide reduces annealing temperature by about 0.62° C. for every 1% increase in formamide concentration; and (d) the longer the probe, the less specific hybridization. Table 2 of U.S. Pat. No. 6,440,683 discloses examples of stringency conditions. One of skill in the art will be familiar with using comparable stringency conditions to evaluate and compare the formation of complexes between a sample nucleotide of a tissue suspected of being diseased (for example, colon cancer or pancreatic cancer) or a normal sample, and a nucleotide such as, for example, SEQ ID NO:1, and a fragment thereof, such as a probe.

A further reference for hybridization conditions is Sambrook, J. et al, 1989, *Molecular Cloning: A Laboratory Manual,* Cold Spring Harbor Laboratory Press, Cold Spring Harbor, N.Y., Chapter 9, as known to those of skill in the art.

The subgenomic polynucleotides can be used to compare related genes in normal control tissue and suspected diseased tissue by any means known in the art. For example, the NRG4 gene or mRNA from a suspected diseased tissue can be sequenced and compared with the NRG4 gene or mRNA sequence in the normal tissue. The NRG4-related genes, or portions thereof, in the two tissues are amplified, for example using nucleotide primers based on the nucleotide sequence of NRG4, using the polymerase chain reaction. The amplified genes or mRNAs or portions thereof are hybridized to nucleotide probes selected from the same NRG4 nucleotide sequence and sequenced. A difference in the nucleotide sequence of the NRG4-related gene in the tissue suspected of being diseased compared with the normal nucleotide sequence suggests a role of the NRG4 protein in the disease, and provides a lead for preparing a therapeutic agent. The nucleotide probes or nucleotides incorporated during sequencing are labeled by a variety of methods, such as radiolabeling, biotinylation, or labeling with fluorescent or chemiluminescent tags, and detected by standard methods known in the art.

Alternatively, NRG4 mRNA levels in normal and suspected diseased tissues are compared. PolyA$^+$ RNA is isolated from the two tissues as is known in the art. For example, one of skill in the art can readily determine differences in the size or amount of NRG4-related mRNA transcripts between the two tissues by Northern blot analysis, primer extension, S1 nuclease protection, reverse transcription-polymerase chain reaction (RT-PCR), or in situ hybridization using polynucleotide probes corresponding to NRG4 or complement thereof. Increased or decreased expression of an NRG4-related mRNA in a tissue sample suspected of being diseased, compared with the expression of the same NRG4-related mRNA in a normal tissue, suggests that the NRG4 protein or lack thereof has a role in the disease, and also provides a lead for preparing a therapeutic agent.

NRG4 gene expression can also be examined using polynucleotide arrays. Polynucleotide arrays provide a high throughput technique that can assay a large number of polynucleotide sequences in a sample. This technology can be used as a diagnostic and as a tool to test for differential expression of an encoded protein. Techniques for constructing arrays and methods of using these arrays are described in EP No. 0 799 897; PCT. No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734, which are incorporated by reference.

Antibodies which bind NRG4 and/or variant polypeptides can be used in diagnosing and determining the prognosis of cancer, tumor progression, hyperproliferative cell growth or accompanying biological and physical manifestations. These antibodies may be monoclonal, polyclonal or single chain antibodies and are produced by methods well known in the art.

Any method known in the art can be used to compare NRG4 proteins from normal control samples and suspected diseased samples. The size of the protein in the two tissues can be compared, for example, using anti-NRG4 antibodies to detect NRG4 polypeptides by Western blot. Alterations in the size of the NRG4 protein in a tissue suspected of being diseased compared with the size in a normal control sample indicate the protein is abnormal, possibly due to truncation, deletion or altered post-translational modification. Size alterations are indicative that NRG4 has a role in the disease and provide a lead for preparing a therapeutic agent. Other changes, such as protein expression levels and subcellular localization can also be detected immunologically, for example by using antibodies directed against NRG4 for Western blot or immunofluorescence. A higher or lower level of NRG4 protein in a tissue suspected of being diseased, or in conditioned media of cells derived from said tissue, or in blood from a patient suspected of being diseased, compared with the level in a normal control sample, is indicative that NRG4 has a role in the disease and provides another lead for preparing a therapeutic agent. Similarly, changes in subcellular localization of NRG4 protein also indicate NRG4 has a role in the disease.

Reagents specific for NRG4 polynucleotides and polypeptides, such as antibodies and nucleotide probes, can be supplied in a kit for detecting the presence of an expression product in a biological sample. The kit can also contain buffers or labeling components, detection reagents, and instructions for using reagents to detect and quantify expression products in biological samples and control normal biological samples. Normal biological samples may be in any form suitable for the particular method of detection utilized by the kit. For example, normal biological samples can be polynucleotides, polypeptides, cellular extracts or tissue sections.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

All patents and publications cited herein are incorporated by reference herein.

EXAMPLES

Example 1

Tissue Distribution of NRG4

In order to determine the tissue distribution of NRG4 (the DNA and amino acid sequences for which are shown in SEQ ID NOs:1 and 2, respectively), quantitative PCR was performed on a number of normal and tumor cells lines, particularly colorectal and pancreatic cell lines. Briefly, quantitative real-time PCR was performed on either commercially available tissue RNA (Ambion, Stratagene) or on RNA isolated from the desired cells using a Roche Isolation kit according to the manufacturer's instructions. One microgram of RNA was then used as a template to synthesize a first strand cDNA using MMLV reverse transcriptase (Ambion) and the manufacturer's buffer and recommended concentrations of oligodeoxynucleotides (oligo dTs), nucleotides, and RNAsin. Specifically, for each 20 µl reaction, 1 µg of RNA was placed into a sterile tube and water was added to a final volume of 12.5 µl. To each tube was added 7.5 µl of a buffer/enzyme mix, prepared by mixing 2.5 µl H$_2$O, 2 µl 10× reaction PCR buffer (Ambion), 1 µl oligo dT (20 pmol), 1 µl dNTP mix (10 mM each), 0.5 µl RNAsin (20 U) and 0.5 µl MMLV reverse transcriptase (50 U). The contents of the reaction were mixed and the reaction was incubated at 42° C. for 1 hour, then centrifuged prior to amplification.

The first stand cDNA generated as described above was then used as a template for quantitative real-time PCR using the GeneAmp™ 5700 Sequence Detection System (PE Biosystems) as recommended by the manufacturer. NRG4 sequences were amplified with the forward primer 5'-ACAGATCACGAAGAGCCCTGTGG-3' (SEQ ID NO:3) and reverse primer 5'-GGTACTGCTCGTCTCTACCAGGTTG-3' (SEQ ID NO:4). Small differences in amounts of total template in the first-strand cDNA reaction were eliminated by normalizing to the amount of actin or GusB sequences amplified in separate quantitative PCR reactions. The forward primer for actin sequence amplification was 5'-CGGGAAATCGTGCGTGACATTAAG-3' (SEQ ID NO:5) and the reverse primer 5'-TGATCTCCTTCTGCATCCTGTCGG-3' (SEQ ID NO:6). The forward primer for GusB sequence amplification was 5'-CCTTTTGCGAGAGAGATACT-3' (SEQ ID NO:7) and the reverse primer was 5'-CCTTAGTGTTCCCTGCTAG-3' (SEQ ID NO:8). An amplification mixture was prepared by mixing in the following order: 8.7 µl water, 12.5 µl 2×SYBR green mix (Molecular Probes), 0.9 µl of each primer (5 pmol/µl each) and 2 µl of template RT product reaction described in the preceding paragraph, bringing the total volume to 20 µl. Amplification on the PE Biosystems 5700 was carried out according to standard protocol. SYBR Green (Molecular Probes, Eugene, Oreg.) is a dye that fluoresces when bound to double stranded DNA. As double stranded PCR product is generated during amplification, the fluorescence from SYBR Green increases. PCR products were quantified based on the cycle at which the amplification entered the linear phase of amplification in comparison to an internal standard, and using software supplied by the manufacturer.

Figure 2:
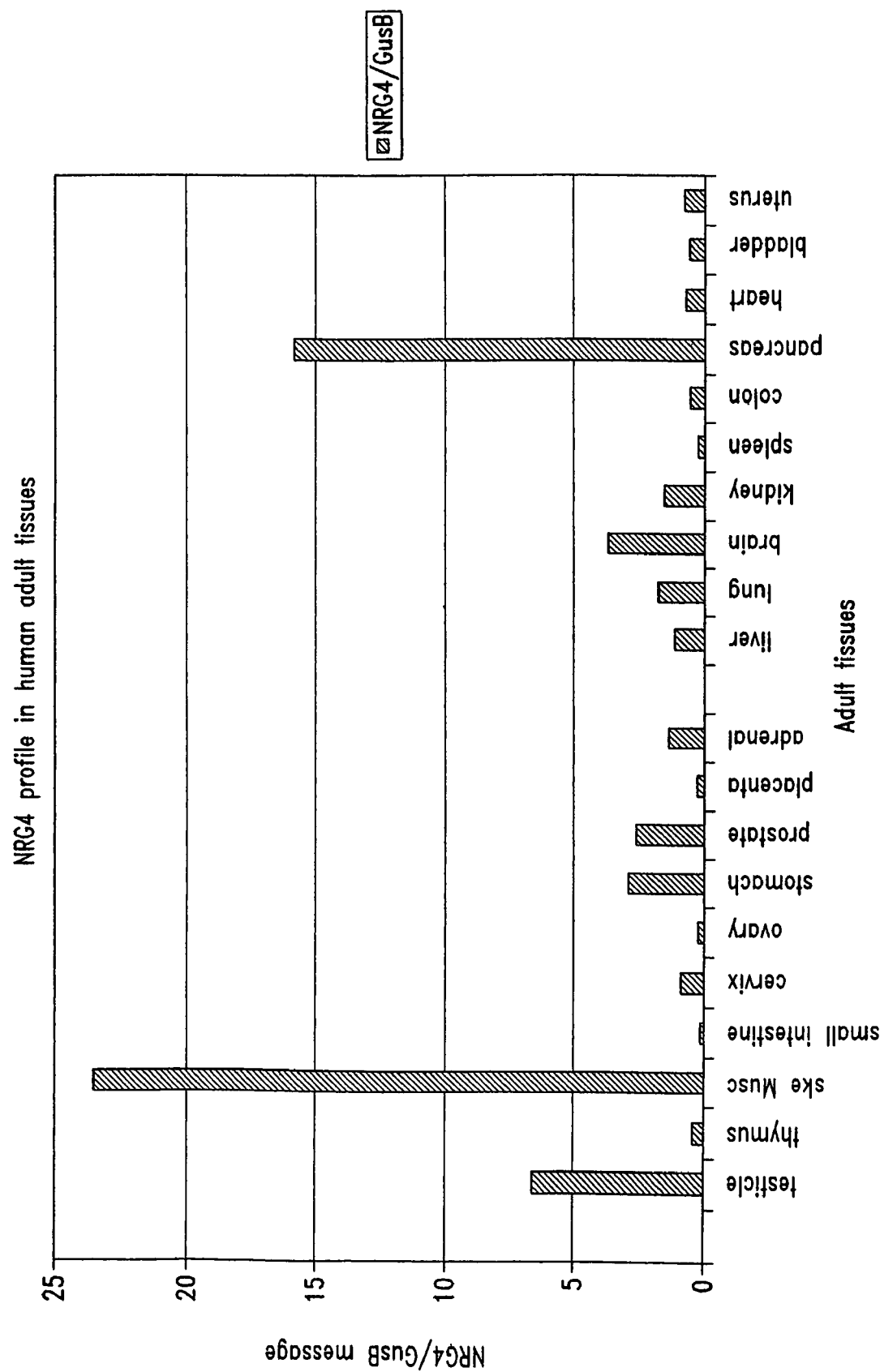
FIG. 2 is a bar graph showing expression of NRG4 in human adult tissues, relative to GusB expression.

Real time PCR results demonstrated that approximately 50% of the colon/colorectal cell lines examined exhibited up-regulation of NRG4 mRNA when compared to normal colon. (FIG. 1, Table 2) Results also revealed down-regulation of NRG4 mRNA in 100% of pancreatic cancer cell lines tested. (Table 1.) Of the normal tissues tested (testicle, thymus, skeletal muscle, small intestine, cervix, ovary, stomach, prostate, placenta, adrenal gland, liver, lung, brain, kidney, spleen, colon, pancreas, heart, bladder, and uterus) low level expression was only seen in testicle, skeletal muscle and pancreas. (FIG. 2.)

TABLE 1

Expression in pancreatic cancer cell lines

| Cell Line | ATCC number | Cell type | NRG4 expression relative to GusB expression |
|---|---|---|---|
| Normal pancreas | | | 14.5 |
| AsPC-1 | CRL-1682 | Adenocarcinoma | 4.1 |
| Capan1 | HTB-79 | Metastatic adenocarcinoma | 3.2 |
| MiaPaCa2 | CRL-1420 | Primary cell line | 0.1 |
| Panc1 | CRL-1469 | Primary cell line | 0.8 |
| PL45 | CRL-2558 | Ductal adenocarcinoma | 0.1 |

TABLE 2

Expression in colon cancer cell lines

| Cell line | ATCC number | Cell type | NRG4 expression relative to GusB expression |
|---|---|---|---|
| Colon | | | 0.9 |
| Colo320DM | CCL-220 | Adenocarcinoma | 3.7 |
| Km12C | CMCC 11825 | Colon-low metastatic potential | 3.2 |
| Km12L4 | CMCC 11611 | Colon-high metastatic potential | 4.45 |
| LoVo | CCL-229 | Colorectal carcinoma | 0.1 |
| HCT116 | CCL-247 | Colorectal carcinoma | 1.95 |

Example 2

Immunohistochemical Analysis of NRG4 Expression

To determine if there is differential expression of NRG4 protein in cancer versus normal tissues, immunohistochemistry is performed on colon and pancreatic tissues from normal and cancer patients using monoclonal and/or polyclonal antibodies against NRG4.

In order to perform this analysis, the slides containing paraffin-embedded sections of interest are de-waxed and rehydrated with xylene followed by alcohol and phosphate-buffered saline (PBS), prior to antigen imaging. The slides are immersed in 1× Citra Plus Solution and placed in a pressure cooker and heated for 5 minutes. After cooling, the slides are rinsed with deionized water and blocked in 3% $H_2O_2$ for 10 minutes at room temperature. The slides are washed with deionized water and PBS and blocked with avidin at room temperature for 10 minutes. Biotin is then applied to the slide for 10 minutes at room temperature after washing in PBS to remove the avidin. Post-biotin treatment, the slides are rinsed in PBS and immersed in protein block (1× PowerBlock) for 8 minutes at room temperature. After rinsing with PBS, 350 µl of anti-NRG4 antibody or control antibody is applied on the section and incubated for 1 hour at room temperature. The slides are then washed three times with PBS for 3-5 minutes per wash. The secondary link (BioGenex™ Multi-Link™) is applied for 10 minutes at room temperature and then washed 3 times with PBS.

To visualize the antigen, BioGenex™ HRP label is applied to the sections for 10 minutes at room temperature and then removed by washing with PBS. BioGenex™ $H_2O_2$ substrate is added at room temperature for 10 minutes, followed by washing with deionized water. The sections are then counterstained with hematoxylin for 1 minute at room temperature. The slides are then rinsed twice with water, incubated in PBS for 1 minute and rinsed once again with water to remove the PBS. A drop of BioGenex™ Super Mount is applied to the section and air-dried overnight at room temperature. The slides are analyzed by microscopy for localization of NRG4.

Example 3

Antisense Regulation of NRG4 Expression

Additional functional information on NRG4 is generated using antisense knockout technology. NRG4 expression in cancerous cells is further analyzed to confirm the role and function of NRG4 polypeptides in tumorigenesis, e.g., in promoting a metastatic phenotype.

A number of different oligonucleotides complementary to NRG4 mRNA are designed as potential antisense oligonucleotides and tested for their ability to suppress expression of NRG4. The ability of each designed antisense oligonucleotide to inhibit gene expression is tested through transfection into SW620 or Km12L4 colon colorectal carcinoma cells. For each transfection mixture, a carrier molecule, preferably a lipitoid or cholesteroid, is prepared to a working concentration of 0.5 mM in water, sonicated to yield a uniform solution, and filtered through a 0.45 µm PVDF membrane. The antisense or control oligonucelotide is then prepared to a working concentration of 100 µM in sterile Millipore water. The oligonucleotide is further diluted in OptiMEM™ (Gibco BRL), in a microfuge tube, to 2 µM, or approximately 20 µg oligo/ml of OptiMEM™. In a separate microfuge tube, lipitoid or cholesteroid, typically in the amount of about 1.5-2 nmol lipitoid/µg antisense oligonucleotide, is diluted in the same volume of OptiMEM™ used to dilute the oligonucleotide. The diluted antisense oligonucleotide is then immediately added to the diluted lipitoid or cholesteroid and mixed by pipetting up and down. The oligonucleotide is then added to the cells to a final concentration of 30 nM.

The level of the NRG4 mRNA is quantitated in the transfected cancer cell lines using the Roche LightCycler™ real-time PCR machine. Values for the NRG4 mRNA are normalized versus an internal control (e.g., beta-actin). For each 20 µl reaction, extracted RNA (generally 0.2-1 µg total) is placed in a sterile 0.5 or 1.5 ml microcentrifuge tube, and water is added to a total volume of 12.5 µl. To each tube is added 7.5 µl of a buffer/enzyme mixture, prepared by mixing (in the order listed) 2.5 µl $H_2O$, 2.0 µl 10× reaction buffer (Ambion), 10 µl oligo dT (20 pmol), 1.0 µl dNTP mix (10 mM each), 0.5 µl RNAsin® (20 U) (Ambion, Inc., Hialeah, Fla.), and 0.5 µl MMLV reverse transcriptase (50 U) (Ambion Inc.). The contents are then mixed by pipetting up and down, and the reaction mixture is incubated at 42° C. for 1 hour. The contents of each tube are centrifuged prior to amplification.

An amplification mixture is prepared by mixing in the following order to obtain the final concentrations listed for each component: 1×PCR buffer II (10 mM Tris pH 8.3, 50 mM KCl), 3 mM $MgCl_2$, 140 µM each dNTP, 0.175 pmol each oligo, 1:50,000 dilution of SYBR® Green, 0.25 mg/ml BSA, 1 unit Taq polymerase, and $H_2O$ to 20 µl. To each 20 µl aliquot of amplification mixture, 2 µl of template RT is added, and amplification is carried out according to standard protocols. As double stranded PCR product is produced during amplification, the fluorescence from SYBR® Green increases.

Example 4

Effect of NRG4 Expression on Proliferation

The effect of NRG4 on proliferation is assessed using antisense oligonucleotides in metastatic breast cancer cell lines (MDA-MB-231 ("231")), SW620 or Km12L4 colon colorectal carcinoma cells, or 847 human immortal fibroblast cells. Transfection is carried out as described above in Example 3.

Cells are plated to approximately 50-80% confluence in 96-well dishes. Antisense or reverse control oligonucleotide is diluted to 2 µM in OptiMEM™ and added to OptiMEM™ into which the delivery vehicle, lipitoid 116-6 in the case of SW620 cells or 1:1 lipitoid 1:cholesteriod 1 in the case of MDA-MB-231 cells, is diluted. The oligo/delivery vehicle mixture is then further diluted into medium with serum on the cells. The final concentration of oligonucleotide for all experiments is 300 nM, and the final ratio of oligo to delivery vehicle for all experiments is 1.5 nmol lipitoid/µg oligonucleotide. Cells are transfected overnight at 37° C. and the transfection mixture is replaced with fresh medium the next morning. The cells are counted at various time points, and cell proliferation is determined using CyQuant™ (Molecular Probes) according to the manufacturer's protocol.

Example 5

Effect of NRG4 Expression on Colony Formation

The effect of NRG4 expression on colony formation is tested in a soft agar assay. Soft agar assays are conducted by first establishing a bottom layer of 2 ml of 0.6% agar in media plated fresh in each well of a 6-well plate within a few hours of layering on the cells. The cell layer is formed on top of the bottom layer by first obtaining cells transfected as described above from plates using 0.05% trypsin. The cells are washed twice in media, counted in a Coulter Counter™, and re-suspended to $10^6$ per ml in media. 10 µl aliquots are placed with media in 96-well plates (to check viable cell count with WST1), or diluted further for soft agar assay. 2000 cells are plated in 800 µl 0.4% agar in duplicate wells above 0.6% agar bottom layer. After the cell layer agar solidifies, 2 ml of media is dribbled on top and antisense or reverse control oligo is added without delivery vehicles. Fresh media and oligos are added every 3-4 days. Colonies are formed in 10 days to 3 weeks. Fields of colonies are counted by eye. Wst-1 metabolism values can be used to compensate for small differences in starting cell number. Larger fields can be scanned for visual record of differences.

All publications and patent documents mentioned in the specification are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of diagnosing pancreatic cancer in a patient, said method comprising:
   (a) determining the amount of a polypeptide comprising the amino acid sequence of SEQ ID NO: 2 in a sample of pancreatic tissue from the patient;
   (b) determining the amount of said polypeptide in a sample of normal pancreatic tissue; and
   (c) determining that there is an indication that the patient has pancreatic cancer if the amount of said polypeptide in said sample of pancreatic tissue from the patient is less than the amount of said polypeptide in said sample of normal pancreatic tissue.

2. A method of diagnosing pancreatic cancer in a patient, said method comprising:
   (a) determining the amount of a polypeptide comprising the amino acid sequence of SEQ ID NO: 2 in a sample of pancreatic tissue from the patient; and
   (b) determining if there is an indication that the patient has pancreatic cancer by comparing the amount of said polypeptide in said sample of pancreatic tissue from the patient and the amount of said polypeptide in a sample of normal pancreatic tissue,
   wherein there is an indication that the patient has pancreatic cancer when the amount of said polypeptide in said sample of pancreatic tissue from the patient is less than the amount of said polypeptide in the sample of normal pancreatic tissue.

3. The method of claim 1 or 2, wherein the amount of said polypeptide in the sample of pancreatic tissue from the patient is determined by immunoassay.

4. The method of claim 3, wherein said immunoassay comprises contacting said sample or a fraction thereof with an antibody or antigen binding fragment thereof that specifically binds to a polypeptide selected from the group consisting of a polypeptide comprising the amino acid sequence of SEQ ID NO: 2 and a polypeptide comprising the amino acid sequence of amino acids 4 to 50 of SEQ ID NO: 2.

5. The method of claim 4, wherein said antibody is selected from the group consisting of a polyclonal antibody, a monoclonal antibody, a chimeric antibody, a humanized antibody, and a single chain antibody.

6. The method of claim 4, wherein said antigen binding fragment is a Fab or a F(ab')$_2$.

7. The method of claim 4, wherein said antibody or antigen binding fragment thereof is detectably labeled.

8. The method of claim 7, wherein said antibody or antigen binding fragment thereof is detectably labeled with an enzyme, a radionuclide, a luminescent moiety, or a fluorescent moiety.

9. The method of claim 4, wherein said antibody or antigen binding fragment thereof is biotinylated.

10. The method of claim 3, wherein said immunoassay is selected from the group consisting of an immunohistochemical analysis, an ELISA, a radioimmunoassay, a Western blot analysis, and a fluorescence-activated cell analysis.

11. A method of diagnosing pancreatic cancer in a patient, said method comprising:

(a) determining the amount of a mRNA molecule encoding a polypeptide comprising the amino acid sequence of SEQ ID NO: 2 in a sample of pancreatic tissue from the patient;

(b) determining the amount of said mRNA in a sample of normal pancreatic tissue; and (c) determining that there is an indication that the patient has pancreatic cancer if the amount of said mRNA in said sample of pancreatic tissue from the patient is less than the amount of said mRNA in said sample of normal pancreatic tissue.

12. A method of diagnosing pancreatic cancer in a patient, said method comprising:

(a) determining the amount of a mRNA molecule encoding a polypeptide comprising the amino acid sequence of SEQ ID NO: 2 in a sample of pancreatic tissue from the patient; and (b) determining if there is an indication that the patient has pancreatic cancer by comparing the amount of said mRNA molecule in said sample of pancreatic tissue from the patient and the amount of said mRNA molecule in a sample of normal pancreatic tissue, wherein there is an indication that the patient has pancreatic cancer when the amount of said mRNA molecule in said sample of pancreatic tissue from the patient is less than the amount of said mRNA molecule in the sample of normal pancreatic tissue.

13. The method of claim 11 or 12, wherein the amount of said mRNA molecule in the sample of pancreatic tissue from the patient is determined by an assay selected from a Northern blot analysis, a primer extension analysis, an S1 nuclease protection analysis, a RT-PCR assay, and an in situ hybridization assay.

14. The method of claim 11 or 12, wherein the amount of said mRNA molecule is determined by contacting said sample or a fraction thereof with a polynucleotide probe that hybridizes to said mRNA.

15. The method of claim 14, wherein said polynucleotide probe is detectably labeled.

16. The method of claim 15, wherein said polynucleotide probe is detectably labeled with a radioactive moiety, a chemiluminescent moiety, or a fluorescent moiety.

17. The method of claim 14, wherein said polynucleotide probe is biotinylated.

* * * * *